(12) United States Patent
Abraham-Fuchs et al.

(10) Patent No.: US 6,712,763 B2
(45) Date of Patent: Mar. 30, 2004

(54) DEVICE FOR FINDING THE TRIGGERS OF PAROXYSMALLY OCCURRING ILLNESSES

(75) Inventors: Klaus Abraham-Fuchs, Erlangen (DE); Eva Rumpel, Erlangen (DE); Kai-Uwe Schmidt, Erlangen (DE)

(73) Assignee: Siemens AG, Munich (DE)

( * ) Notice: Subject to any disclaimer, the term of this patent is extended or adjusted under 35 U.S.C. 154(b) by 13 days.

(21) Appl. No.: 10/058,988

(22) Filed: Jan. 30, 2002

(65) Prior Publication Data
US 2002/0184177 A1 Dec. 5, 2002

(30) Foreign Application Priority Data
Jan. 30, 2001 (DE) .......................... 101 03 947

(51) Int. Cl.[7] ............................... A61B 5/00
(52) U.S. Cl. ........................ 600/300; 128/923
(58) Field of Search ................. 600/300, 301; 128/420–925; 705/2, 3

(56) References Cited

U.S. PATENT DOCUMENTS

| 3,841,309 A | | 10/1974 | Salter et al. | |
| 4,844,086 A | | 7/1989 | Duffy | |
| 5,251,626 A | | 10/1993 | Nickolls et al. | |
| 5,660,181 A | * | 8/1997 | Ho et al. | 128/925 |
| 5,857,980 A | | 1/1999 | Wilson | |
| 6,101,409 A | | 8/2000 | Swanson et al. | |
| 6,527,712 B1 | * | 3/2003 | Brown et al. | 600/300 |

FOREIGN PATENT DOCUMENTS

| DE | 198 25 191 A1 | 12/1999 | | |
| DE | 198 42 046 A1 | 3/2000 | | |
| EP | 622625 A2 | * 11/1994 | .......... | G01N/21/35 |
| WO | WO 97/04712 | 2/1997 | | |
| WO | WO 97/20496 | 6/1997 | | |
| WO | 99/63886 | 12/1999 | | |

OTHER PUBLICATIONS

Chen et al, Data Analysis, Wiley Encyclopedia of Electrical Engineering and Electronics Engineering Online, Dec. 1999, pp. 1–7.*
Pomykalski et al, Expert Systems, Wiley Encyclopedia of Electrical Engineering and Electronics Engineering Online, Dec. 1999, pp. 1–28.*
Fein et al, The Climatic Factors in the Etiology of Allergic Diseases, Journal of Asthma Research, vol. 3, No. 1, Sep. 1965, pp. 17–23.*
Neugut et al, Anaphylaxis in the United States: An Investigation into its Epidemiology, Archives of Internal Medicine, Jan. 2001, vol. 161, pp. 15–21.*
László Czinege, "Multi–Channel EEG Activity Correlation Analysis to Detect the Onset of Cerebral Ischemia," Engineering in Medicine and Biology Society, 1994, pp. 1230–1231.

* cited by examiner

Primary Examiner—Eric F. Winakur
Assistant Examiner—David McCrosky
(74) Attorney, Agent, or Firm—Young & Thompson

(57) ABSTRACT

Device for finding unknown, multifactorial triggers of paroxysmally occurring illnesses, which is coupled to an electronic patient file and/or, if appropriate, spatially distributed databases, a comparison and evaluation device carrying out, after a paroxysm, a correlation analysis in order to search for typical patterns in the temporal occurrence of the stored data elements.

20 Claims, 4 Drawing Sheets

| Event | Time | | Value as appropriate | Type |
|---|---|---|---|---|
| Headache | 02.15.98 14:00 | 1.0 | severe | Anamnesis |
| Cold | 02.16.98 15:00 | 1.0 | | Diagnosis |
| Medication X prescribed | 02.16.98 15:00 | 1.0 | | Prescription |
| Medication X taken | 02.27.98 0:00 | 1.0 | | Measure |
| Medication X taken | 02.28.98 0:00 | 1.0 | | Measure |
| Medication X taken | 03.01.98 0:00 | 1.0 | | Measure |
| Blood pressure | 03.01.98 19:00 | 0.3 | 120/60 | Measurement |
| Migraine attack | 03.04.98 11:00 | 1.0 | | Diagnosis |
| Medication Y prescribed | 03.04.98 17:00 | 1.0 | | Prescription |
| Period | 03.05.98 7:00 | 1.0 | | Anamnesis |
| Cancer screening | 03.07.98 9:00 | | | Anamnesis |
| Cancer screening | 03.07.98 11:00 | | | Measurement |
| Blood pressure | 03.08.98 19:00 | 0.6 | 95/130 | Measurement |
| Blood sugar test | | | 80 mg/dl | Measurement |
| Diarrhoea | | | slight | Anamnesis |
| Blood pressure | 03.15.98 19:00 | 0.7 | 95/130 | Measurement |
| Suspected fracture of the shin bone | 03.20.98 9:00 | 1.0 | | CT scan |
| Fracture of the left shin bone | 03.20.98 11:00 | 1.0 | | Diagnosis |
| Fracture of the left shin bone: plaster | 03.20.98 13:00 | 1.0 | | Prescription |
| Blood cholesterol | | | | Measurement |
| Blood pressure | 03.23.98 19:00 | 0.6 | 95/130 | Measurement |
| Blood pressure | 03.30.98 19:00 | 0.2 | 130/90 | Measurement |
| Blood pressure | 03.23.98 0:00 | 0.6 | 130/90 | Measurement |
| Stress, Jet lag | 03.31.98 0:00 | | | Anamnesis |
| Medication X taken | 03.31.98 0:00 | 1.0 | | Measure |
| Medication X taken | 04.01.98 0:00 | 1.0 | | Measure |
| Period Migraine attack | 04.01.98 7:00 | 1.0 | | Anamnesis |
| Migraine attack | 04.02.98 0:00 | 1.0 | | Diagnosis |
| Blood pressure | 04.07.98 0:00 | 05. | 130/90 | Measure |
| Fracture of the left shin bone: walking plaster | 04.10.98 0:00 | | | Prescription |

FIG. 2A

| Blood pressure | 04.14.98 0:00 | 0.6 | 130/90 | Measurement |
|---|---|---|---|---|
| Blood pressure | 04.21.98 0:00 | 0.6 | 130/90 | Measurement |
| Period | 04.28.98 7:00 | 1.0 | | Anamnesis |
| Vaginal itch, inflammation | 05.02.98 11:00 | | | Anamnesis |
| Lab test for mycosis | 05.02.98 11:00 | | | Measurement |
| Vaginal mycosis | 05.02.98 11:00 | | | Diagnosis |
| Medication A | 05.02.98 11:00 | | | Prescription |
| Blood pressure | 04.28.98 0:00 | 0.5 | 130/90 | Measurement |
| Blood pressure | 05.05.98 0:00 | 0.7 | 130/90 | Measurement |
| Blood pressure | 05.12.98 0:00 | 0.3 | 130/90 | Measurement |
| Blood pressure | 05.19.98 0:00 | 0.7 | 130/90 | Measurement |
| Period | 05.23.87 7:00 | 1.0 | | Anamnesis |
| Blood pressure | 05.26.98 0:00 | 0.6 | 130/90 | Measurement |
| Fracture of the left shin bone: plaster removed | | | | Prescription |
| Blood pressure | 06.02.98 0:00 | 0.6 | 130/90 | Measurement |
| Blood pressure | 06.09.98 0:00 | 0.5 | 130/90 | Measurement |
| Blood pressure | 06.15.98 0:00 | 0.4 | 130/90 | Measurement |
| Influenzal infection | | | | Diagnosis |
| Medication Z | | | | Prescription |
| Fever | | | 39 degrees | Measurement |
| Fever | | | 38.5 degrees | Measurement |
| Fever | | | 38 degrees | Measurement |
| Fever | | | 37.5 degrees | Measurement |
| Blood pressure | 06.22.98 0:00 | 0.3 | 130/90 | Measurement |
| Follow-up investigation vaginal mycosis | 06.23.98 0:00 | | | Measurement |
| Medication X taken | 06.23.98 0:00 | 1.0 | | Measure |
| Period | 06.23.98 7:00 | 1.0 | | Anamnesis |
| Migraine attack | 06.24.98 0:00 | 1.0 | | Diagnosis |

FIG 2B

DEVICE FOR FINDING THE TRIGGERS OF PAROXYSMALLY OCCURRING ILLNESSES

BACKGROUND OF THE INVENTION

The invention relates to a device for finding unknown, multifactorial triggers of paroxysmally occurring illnesses such as, for example, epilepsy or neurodermatitis or allergic reactions, which is coupled to an electronic patient file and/or, if appropriate, spatially distributed databases.

DESCRIPTION OF THE RELATED ART

Various illnesses such as epilepsy or neurodermatitis or else allergic reactions are distinguished in that although they can be diagnosed indubitably on the basis of their external expression, it remains extremely problematic nevertheless to identify the precise trigger for the ever recurring fits. The search for the causal relationship is rendered difficult, in particular, when the triggering impetus is represented not by a substance or situation, but by the combination of a plurality of factors. Given—at a conservative estimate—20,000 allergenic substances, this results in such an incomprehensibly large number of possibilities that testing for them is neither possible nor acceptable to the patient. By contrast, the success of a simple observation is limited, in addition, by the fact that months and years typically pass between individual paroxysms.

SUMMARY OF THE INVENTION

It is therefore the object of the invention to create a device for finding unknown multifactorial triggers of paroxysmally occurring illnesses which manages without complicated immune tests.

Provided according to the invention for achieving this object is a device of the type mentioned at the beginning with a comparison and evaluation which carries out, after a paroxysm, a correlation analysis, for example a principal component analysis, a cluster algorithm or else an evaluation with the aid of an associative memory in order to search for typical patterns in the temporal occurrence of the stored data elements.

WO 97/20496 A1 has already disclosed a device with the aid of which the aim is to compile an automatic medical diagnosis and, if appropriate, to devise contraindicant treatment strategies, there being stored in a first database correlations of a multiplicity of illnesses with a multiplicity of indicators which are associated with each of these illnesses, while a second database includes human experimental test results relating to each indicator, the test results of a patient then being compared with the second database, in order to determine the level of presence of each indicator. Subsequently, these levels of presence are compared with the data of the first database in order to obtain a pattern from which the presence of one or other illness results.

However, in this case there is a basic difference from the comparison and evaluation device according to the invention, since the very words indicators denote something different in the present application than in the case of the cited WO 97/20496 A1. The indicators in that printed publication relate to specific symptoms which are associated with an illness, that is to say forms of expression of the illness itself, whereas indicators in the sense of the present application are understood as triggering factors which lead, mostly in conjunction with further factors, to the triggering of a paroxysmal event, that is to say an epileptic fit or a migraine attack. In the case of WO 97/20496 A1, the symptoms denoted as indicators are evaluated for the patient in an automated form, in order to infer a specific illness from the symptoms, that is to say in order to make a diagnosis of an illness. In the present application, the aim is for a completely evident illness, to be precise a specific paroxysmal disease such as epilepsy, migraine attacks or the like, to be analyzed on the basis of the respective prehistories in the diurnal cycle of the paroxysmal patient as to which causes respectively trigger the paroxysm with this patient. However, on the one hand, these are entirely different starting points and, on the other hand, completely different means of solution are employed.

All the available data from various, frequently also spatially distributed, databases such as an electronic patient record and, in a particularly advantageous fashion, also an electronic patient diary are brought together and investigated for their temporal relationship with the documented paroxysms. The correlation analysis carried out according to the invention is capable of detecting typical patterns in the temporal occurrence of the data elements and thereby of identifying substances or situations triggering a paroxysm.

It has proved to be particularly expedient in this regard to connect the device according to the invention to a weather database, since climatic phenomena are very frequently the cause or contributory cause of paroxysmal pathological fits.

In addition to the patient diary, which is very important for the functioning of the inventive automated finding of the triggers of the paroxysmally occurring illnesses, and in which self-observations by the patient are recorded, that is to say, for example, what he respectively does, whether he is in the open air or indoors and so on, something which can be significant, for example, with regard to the identification of flying pollen as the cause of a paroxysm, it is also possible for entries by the staff of the hospital, any nursing services or the like in an electronic patient file to provide important indications of the triggers of illness.

The essence of the present invention resides in this case, by comparison with the previous simple evaluation of the electronic patient files and patient diaries, in the search, possibly conducted without prior knowledge, for patterns in time series of the data elements, in order to use these patterns in the data elements to obtain for the respective paroxysmal fits correlations, and thus indications, of triggering causes.

The advantage of the device according to the invention resides in the fact that a) it takes account of the analysis of the case history over any desired length of time,
b) data which were collected for other purposes can also be included,
c) analysis can include any desired number of factors capable of triggering paroxysms, and
d) multifactorial causes which are as complex as desired can be detected.

The system may be automatically activated with each new entry into one of the databases, and thus permits automated and progressive searching for the factors triggering paroxysms.

In a further configuration of the invention, it can be provided that the device according to the invention is connected to an expert system in which rules are implemented which correspond to the state of medical knowledge on the paroxysmally occurring illnesses and their triggers, such that it is not only that the search, addressed above and performed without prior knowledge, for patterns in time series of the data elements takes place, but that, over and above these patterns, account is also taken of the known expert knowledge on triggering factors that cause paroxysms.

Such a system with an implemented expert system can also—in order to substantiate further or, again, to reject a suspicion arising—request further information from the patient.

In the case of this embodiment with an expert system, as well, the latter may be automatically activated on the occasion of each new entry into the patient diary. With the aid of the expert system, each individual newly added item of information acquires the weight corresponding to its associations, and thereby ensures a disproportionate acquisition of knowledge. The use of expert systems in addition to the comparison and evaluation device for searching for patterns in the time series of the data elements therefore promises to find factors triggering paroxysms more quickly and with more success. Such an expert system can be configured in this case in the form, for example, of a Bayes network or neural network.

BRIEF DESCRIPTION OF THE DRAWINGS

Further advantages, features and details of the invention emerge from the following description of some exemplary embodiments, as well as with the aid of the drawing, in which:

FIG. 2 shows a diary excerpt for a migraine patient over a period in which three migraine attacks have occurred.

DESCRIPTION OF THE PREFERRED EMBODIMENTS

Figure 1:
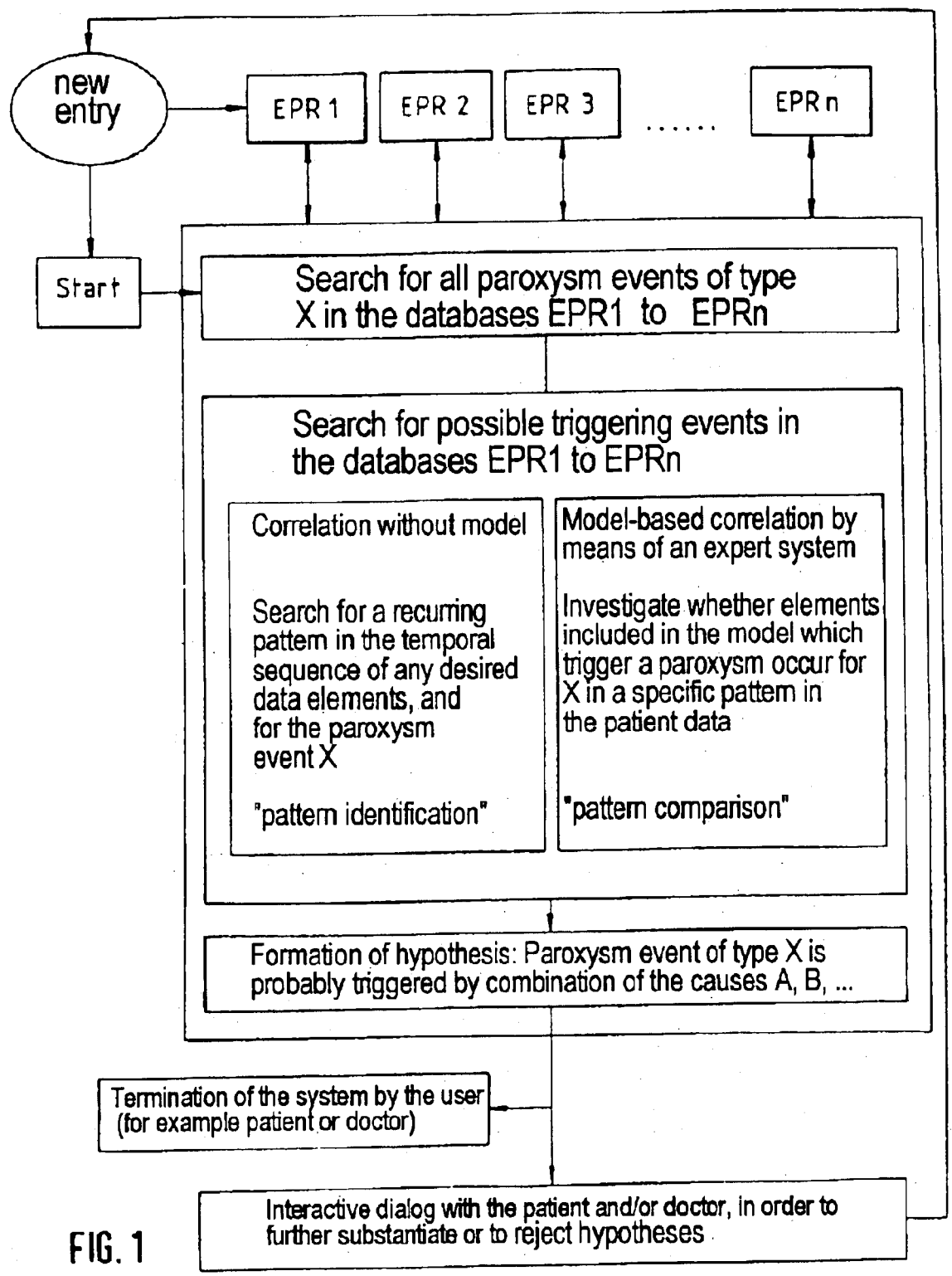
FIG. 1 shows a flowchart of a device according to the invention, without an expert system on the left, and with an expert system on the right.

Numerous mathematical approaches for finding patterns in multidimensional data records are known and can be applied to formulating the problem for this invention. Purely for illustration, mention may be made here of a possible strategy that may be used for detecting patterns.

Event entries in an EPR can be described in a mathematical sense as matrices or vectors, it being possible to consider different value dimensions (type of event, measured value of the event, time of occurrence). Use may also be made as "measured value" of: 1 for an occurrence of the event, 0 for the omission of the event. One possibility for the vectorial description is to represent in relation to a time window (for example within one day) the value of prescribed set of events as event vector E(ti) at the instant ti, for example an event vector with M events (dimension j=1 . . . M).

$$\overline{E(ti)} = \begin{matrix} \text{Blood pressure} & 0.2 \\ \text{Taking of medication } X & 1 \\ \text{Taking of medication } Y & 0 \\ \text{Period} & = 1 \\ \text{Migrane attack} & 0 \\ \text{Stress} & 1 \\ \text{Fever} & 37 \end{matrix} = \begin{matrix} E1 \\ \vdots \\ \vdots \\ \vdots \\ \vdots \\ \vdots \\ EM \end{matrix}$$

The similarity of two event patterns E1 and E2 can then be described mathematically as an angle between the vectors, and this is equivalent to the following mathematical definition or the correlation between the vectors:

$$C = \frac{E1 * E2}{E1 * E2}$$

If the triggers being sought occur, for example as a combination of events in a plurality of sequential time slices (that is to say on a plurality of sequential days before the attack, see example) it is then necessary to combine a plurality of vectors in the relevant time window Tn=T1 . . . TN (eg. 1 . . . 5 days) to form a set ("template"). This set is then pushed as a sliding vector over the evaluation period, and the sliding correlation function is calculated. If the results are distributed randomly in the template and in the examination space, this results in a very noisy correlation function against time with low correlation values. If, however, an event pattern occurs repeatedly inside the template in the evaluation period, this results in a peak of high correlation in the correlation function against time when the template is pushed over the same or a similar event. By using threshold values for the correlation, the occurrence of similar events can be determined automatically with the aid of these peaks.

The calculation of the correlation function against time can be described mathematically in the following fashion using this model:

$$C(ti) = \frac{\sum_{j=1}^{M}\sum_{Tn=1}^{N} E_j(ti+Tn) * E_j(Tn)}{\sum_{j=1}^{M}\sum_{Tn=1}^{N} E_j^2(ti+Tn) * \sum_{j=1}^{M}\sum_{Tn=1}^{N} E_j^2(Tn)}$$

Different strategies can be applied to search automatically for event patterns which are triggers for the paroxysm. It is possible, for example, to pick out a paroxysm, define a time window of 3 days before the paroxysm as a template, search for the occurrence of correlation peaks before further paroxysms and then to reduce the event (=dimension of the vector), combinatorially, in order to filter out the events which have caused the correlation peak. It is possible to use the data sets in the dimensions and periods considered here to calculate correlation functions over long periods (months and years) in a few seconds to fractions of a second, and so this search strategy can be carried out realistically and in an automated fashion.

Figure 3:
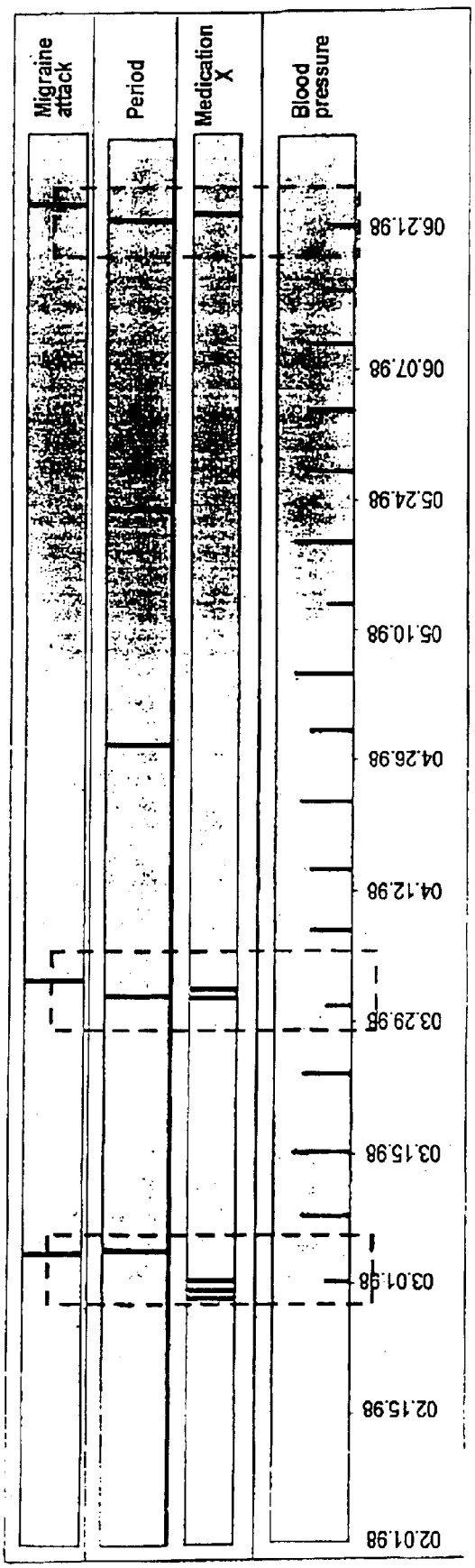
FIG. 3 shows an evaluation diagram on which it can be seen how the respective paroxysm was triggered by a specific indicator group.

In the attached example, it may be seen in FIG. 3 that the combined triggers for a migraine attack on the patient is the taking of the medication X and low blood pressure shortly before the occurrence of the female period. If these events do not occur together, neither does a migraine attack.

What is claimed is:

1. A device for finding unknown, multifactorial triggers of paroxysmally occurring illnesses, which is coupled to an electronic patient file and/or, if appropriate, spatially distributed databases, characterized by a comparison and evaluation device which carries out a correlation analysis in order to search for typical patterns in the temporal occurrence of stored data elements of the patient file and the databases, which patterns are correlated with the occurrence of the paroxysm and includes an analysis of a time interval preceding the occurrence of the paroxysm.

2. The device as claimed in claim 1, characterized in that the correlation analysis is a principal component analysis.

3. The device as claimed in claim 1, characterized in that the correlation analysis includes a cluster algorithm.

4. The device as claimed in claim 1, characterized in that the comparison and evaluation device contains an associative memory.

5. The device as claimed in claim 1, characterized in that it is coupled to an electronic patient diary.

6. The device as claimed in claim 1, characterized in that it is connected to a weather database.

7. The device as claimed in claim 1, characterized in that it is connected to an expert system in which rules are implemented which correspond to the state of medical knowledge on the paroxysmally occurring illnesses and their triggers.

8. The device as claimed in claim 7, characterized in that the expert system includes a Bayes network.

9. The device as claimed in claim 7, characterized in that the expert system includes a neural network.

10. A device for finding a trigger of a paroxysmally occurring illness, comprising:

an electronic patient file of a paroxysmal patient, the patient file including prehistories in diurnal cycles of the paroxysmal patient where, subsequent to the cycles, a trigger causes paroxysm events in the patient; and an analysis component interfaced with stored data elements of the electronic patient file, the analysis component identifying the trigger of the paroxysm events through a correlation analysis, of the stored data elements, for typical patterns in temporal occurrences of the paroxysm events, the analysis component, in identifying the trigger, utilizing stored data elements of the prehistories for time periods immediately preceding the paroxysm events.

11. The device of claim 10, wherein the paroxysmally occurring illness is epilepsy.

12. The device of claim 10, wherein the paroxysmally occurring illness is neurodermatitis.

13. The device of claim 10, wherein the analysis does not consider results of immune tests in the correlation analysis.

14. The device of claim 10, wherein the correlation analysis is one of a main component analysis, a cluster algorithm, and an evaluation with the aid of an associative memory.

15. The device of claim 10, further comprising:

a spatially distributed database interfaced with the analysis component, and wherein the correlation analysis detects patterns in the temporal occurrence of the data elements for identifying substances or situations triggering a paroxysm.

16. The device of claim 15, wherein the distributed database comprises a weather database.

17. The device of claim 10, further comprising:

an expert system interfaced to the analysis component, the expert system comprising rules concerning paroxysmally occurring illnesses and corresponding triggers.

18. The device of claim 10, wherein, the analysis component, in identifying the trigger by utilizing stored data elements for time periods immediately preceding the paroxysm events, correlates events in evaluation periods of a plurality of sequential days before each of the paroxysm events.

19. The device of claim 18, wherein the trigger is identified by an event pattern that occurs repeatedly inside the evaluation periods as peaks of high correlation in a correlation function against time.

20. The device of claim 19, wherein, the analysis component uses a threshold value for the correlation, and the occurrence of the trigger is determined automatically by the peaks exceeding the threshold value.

* * * * *